(12) United States Patent
Polk et al.

(10) Patent No.: US 10,028,504 B1
(45) Date of Patent: Jul. 24, 2018

(54) PYROTECHNIC IODINE SMOKE GENERATION FOR COUNTER BIOLOGICAL APPLICATION

(71) Applicant: U.S. Army Edgewood Chemical and Biological Center, Washington, DC (US)

(72) Inventors: Amee L Polk, Havre de Grace, MD (US); Michael F. Kauzlarich, Edgewood, MD (US); Lisa S. Smith, College Park, MD (US); Nino L. Bonavito, Perry Hall, MD (US); Vipin K. Rastogi, Bel Air, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 30 days.

(21) Appl. No.: 15/136,281

(22) Filed: Apr. 22, 2016

(51) Int. Cl.
*A01N 25/20* (2006.01)
*F42B 12/48* (2006.01)
*A01N 59/12* (2006.01)

(52) U.S. Cl.
CPC ............. *A01N 25/20* (2013.01); *A01N 59/12* (2013.01); *F42B 12/48* (2013.01)

(58) Field of Classification Search
None
See application file for complete search history.

(56) References Cited

U.S. PATENT DOCUMENTS

| | | | | |
|---|---|---|---|---|
| 3,257,801 A | * | 6/1966 | Martinez ................. | C06B 33/02 |
| | | | | 149/19.7 |
| 2010/0252022 A1 | * | 10/2010 | Coffey .................... | C06B 33/12 |
| | | | | 126/263.01 |

OTHER PUBLICATIONS

Clark et al, "The aluminium and iodine pentoxide reaction for the destruction of spore forming bacteria", Physical Chemistry Chemical Papers, 12, 2010. pp. 12653-12657.*
Wang et al., Electrospray formation and combustion characteristics of iodine-containing Al/CuO nanothermite microparticles, Combustion and Flame, 2015, vol. 162, pp. 2823-2829. (Year: 2015).*
Golnaz Bohlouli (Synthesis, characterization, and application of nanothermites for joining, Thesis, University of Waterloo, 2013, p. iii-iv, p. 43-63) (Year: 2013).*

* cited by examiner

*Primary Examiner* — Melissa L Fisher
(74) *Attorney, Agent, or Firm* — Ulysses John Biffoni

(57) ABSTRACT

A biocidal and sporicidal smoke composition(s) using iodine oxide and metal powder is provided. This composition generates iodine gas or smoke as the primary biocidal agent, as well as metal oxides that provide additional biocidal properties. The smoke producing composition is suitable for pressing into canisters of compacted powder at a load pressure range of 1500 to 7500 psi and can be used for decontamination of spaces believed to be contaminated with biological agents. The composition is also suitable for use in hand grenades, smoke pots, rifle grenades, mortars, multiple launch grenades, shoulder fired missiles, and artillery rounds, as well as first responder and commercial biological decontamination applications.

9 Claims, 2 Drawing Sheets

PYROTECHNIC IODINE SMOKE GENERATION FOR COUNTER BIOLOGICAL APPLICATION

GOVERNMENT INTEREST

The invention described herein may be manufactured, used, and licensed by or for the United States Government.

FIELD

The invention relates generally to the design of a pyrotechnically generated iodine aerosol composition for use as an initial standoff decontamination of spaces believed to be contaminated with biological agents. The composition can be produced without the use of organic liquids that add to air pollution, and contains specific chemicals to increase its long term shelf life.

BACKGROUND

Iodine containing compounds are one of the most commonly used antimicrobial agents currently in use (Gottardi, *J Hosp Infect* 1985 Mar; 6 Suppl A:1-11). The influence of the chemical behavior of iodine on the germicidal action of disinfectant solutions containing iodine has been described. J. Hosp. Infect. 6(Suppl. A):1-11; Gottardi W. (1991) *Iodine and iodine compounds in disinfection, sterilization, and preservation.* ed Block S. S. (Lea & Febiger, Philadelphia, Pa.), 4th ed. pp 152-166).

To date there exist no pyrotechnic systems designed to generate iodine vapor from metal fuels and iodine oxides. Other halogenated fumigants, such as chlorine dioxide and methyl bromide, have been shown to be biocidal and sporicidal, however, these fumigants are not pyrotechnically derived, resulting in more complicated production requirements. Low concentrations of iodine and heavy metals have been shown to cause the precipitation of cell proteins, thus resulting in cell death. Oligodynamic metals (copper) cause cell membrane destruction as well as coagulation of cell materials.

These metal/iodine oxide compounds readily and thoroughly react when provided an ignition source to produce iodine vapor and metal oxide. The use of certain metals such as brass (copper/zinc blend), aluminum, copper, iron, and ferrotitanium (iron/titanium blend) provide an additional layer of antimicrobial effect as each of these metals have biocidal properties, as well as their metal oxide being biocidal.

SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Decontamination of areas believed to be contaminated with biological organisms such as organisms used in weapons of mass destruction or in terror attacks is of paramount importance. It is an object to provide a composition that is safe to handle and transport but can be readily converted into a biocidal composition that is suitable to reduce the viability of such target biological organisms. This object is achieved by the combination of an iodine material and a metal powder that is sufficiently reactive with the iodine material to produce an iodine vapor or smoke when subjected by a thermite reaction to an energy sufficient to overcome the activation barrier between the two reactants. As such, a biocidal smoke producing composition is provided that includes: an iodine material in an amount of 50 and 75 percent by weight and a metal powder present at 25 to 50 percent by weight where the iodine containing material and the metal powder are sufficiently reactive to produce a biocidal smoke by a thermite reaction. The two reactants are optionally intermixed at equal parts. The iodine containing material optionally includes iodine pentoxide, iodine monochloride, or iodine trichloride, or combinations thereof. A metal powder is optionally elemental powder, and optionally includes copper, iron, aluminum, brass, ferrotitanium, or combinations thereof. In particular aspects, an iodine containing composition is iodine pentoxide and the metal powder includes iron. The iodine material and the metal are optionally further intermixed with or contacted to a binder, optionally including polyvinylidene chloride resin. The composition optionally further includes a coolant in an amount suitable to reduce the reaction rate between the iodine containing material and the metal. A coolant optionally includes bentonite. The composition is optionally compressed to a sub-detonating loading pressure of 1500 pounds per square inch or greater. In some aspects, the composition is loaded into a dispersant device such as a grenade, smoke pot, floating smoke pot, multiple launch grenade, mortar, shoulder fired missile, or artillery shell.

It is another object to provide methods for decontaminating an area that includes one or more target organisms by subjecting the biocidal smoke producing composition to a force sufficient to induce a reaction between said iodine material and the metal thereby producing iodine gas, and contacting the iodine gas to a target bacterial organism or spore for a time sufficient to reduce the viability of the target bacterial organism or spore. The force is optionally 5000 pounds per square inch or greater. The resulting thermite reaction optionally proceeds at a rate that may be governed by the amount of coolant included in the compositions, optionally for a burn time of 30 to 90 seconds. The target bacterial organism is optionally one or more of *Staphylococcus aureus, Bacillus anthracis, Pseudomonas aeruginosa, Acinetobcter baumannii, Bacillus subtilis, Bacillus globigii, Yersinia pestis, Francisella tularensis, Br. melitensis, Burkholderia pseudamallei, C. botulinum,* and *Burkholderia mallei.* A target organism is optionally a bacterial spore, optionally a spore of *Bacillus anthracis* or *Bacillus thuringiensis* var. *Kurstaki*.

DETAILED DESCRIPTION

Figure 1:
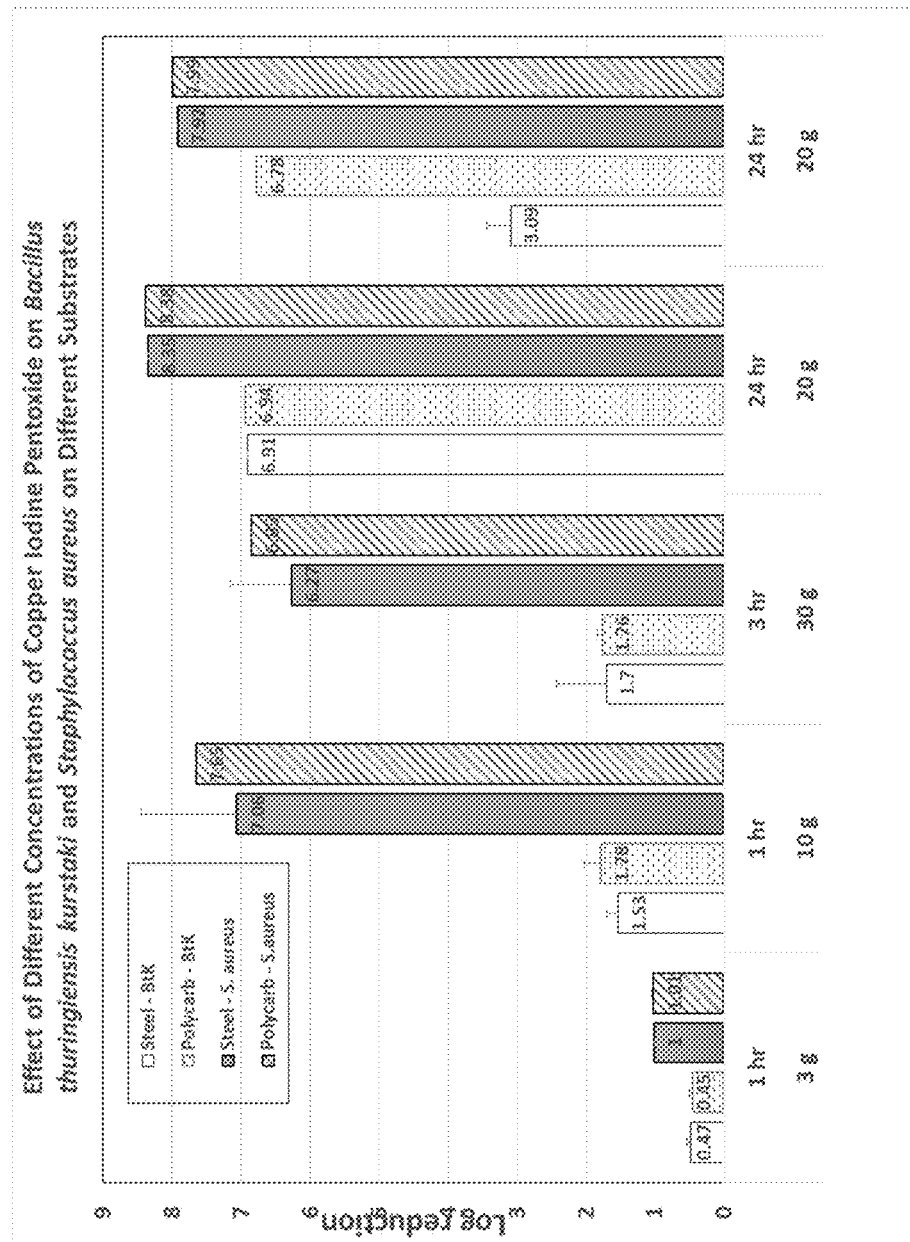
FIG. 1 illustrates the log reduction of *Bacillus thuringiensis* var. *Kurstaki* and *Staphylococcus aureus* relative to control using 20 g of the mixture of copper and iodine pentoxide as the biocidal smoke producing composition and a 24 hour exposure period.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art.

It will be understood that, although the terms "first," "second," "third" etc. may be used herein to describe various elements, components, regions. layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/ or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Provided is a new biocidal smoke composition that utilizes iodine pentoxide as the oxidizer and metal powder as the fuel. The use of metal as the fuel results in the production of iodine vapor; an effective compound in the decontamination of biological agents. The chemical reaction for the production of the biocidal smoke cloud is a simple two reactant/two product system. The metal powder reacts immediately with the oxygen in the iodine material, producing a combination of metal oxide and iodine vapor. The iodine vapor has an immediate and effective biocidal activity that can be used to reduce the viability of or destroy infectious agents or other biological organisms upon contact. As such, the biocidal smoke compositions can be used to decontaminate a contaminated area or volume thereby improving safety.

A biocidal smoke composition is provided that includes an iodine containing material such as iodine oxide or iodine chloride in combination with a metal powder that is suitably reactive with the iodine oxide or iodine chloride so as to produce a biocidal smoke under appropriate conditions. Based on theoretical modeling, metal oxide ($M_xO_y$) and iodine ($I_2$) are the favored products. Modeling also shows low level generation of iodide ion ($I^-$), an easily oxidized species which reacts with oxygen to form iodine ($I_2$), and low levels of oxygen, a non-toxic component of the atmosphere.

An iodine containing material is optionally an iodine oxide or an iodine chloride or combinations thereof. Illustrative examples of iodine oxide include but are not limited to iodine pentoxide, iodine heptoxide, as well as higher order iodine oxides. In some aspects, iodine pentoxide is used. In some aspects an iodine chloride is used as the iodine containing composition. Illustrative examples of iodine chlorides include ICl and $ICl_3$, among others.

The iodine containing composition also includes a reactive metal, optionally in powder form, with suitable reactivity with the iodine containing compound to produce an iodine gas such as a vapor or smoke. Illustrative examples of a metal powder include elemental powders of Fe, Ti, Zn, Al, Cd, Ni, Ca, and combinations thereof. Illustrative examples of metal combinations include brass (alloy of Cu and Zn) and ferrotitanium (e.g. 50:50 atomic ratio of Fe and Ti).

The mass of the components can be varied in such a manner as to adjust the overall rate of the chemical reaction that is represented by the burning rate for a pressed block of biocidal smoke producing composition. This biocidal smoke composition is a robust formulation; a variation of the component ratio of ±2% should not affect its function. Additional coolants may be added to the composition to affect its burning rate. Optionally, the amount of the iodine containing composition is from 50 to 75 percent by weight, or any value or range therebetween. The relative amount of iodine containing composition is optionally 50, 51, 52, 53, 54, 55, 56, 57, 58, 59, 60, 61, 62, 63, 64, 65, 66, 67, 68, 69, 70, 71, 72, 73, 74 or 75 percent by weight. In some aspects, the relative amount of metal powder is 25 to 50 percent by weight, or any value or range therebetween. Optionally, the amount of metal powder is 25, 26, 27, 28, 29, 30, 31, 32, 33, 34, 35, 36, 37, 38, 39, 40, 41, 42, 43, 44, 45, 46, 47, 48, 49, or 50 percent by weight. In some aspects, the iron containing composition and the metal are preset at equal amounts by weight.

The biocidal smoke composition may be formed by combining the iodine containing material and the metal and intermixing the two, either mechanically or by hand. In some aspects, a composition includes one or more binders intermixed with the iodine containing material and the metal. As defined herein, the term "binder" is a synthetic polymer which is used in small quantities (typically 5-10% by weight) to bind together an explosive powder, in this case the iodine containing material and the metal.

Illustrative examples of a binder include hydrophobic resins such as cellulose acetate (CA), cellulose acetate butyrate (CAB), hydroxy- terminated polybutadiene (HTPB), polyurethanes, polyethylene, polyester, polypropylene, polystyrene, polyvinyl chloride, polyvinyl acetate, acryl resin, silicone resin, fluorine-containing resin, vinyl chloride/vinyl acetate copolymer, vinyl chloride/vinylidene chloride copolymer, polystyrene/butadiene copolymer, and the like. Specific illustrative examples of a binder include HYTEMP (polyacrylate elastomer), SARAN (polyvinylidene chloride), nitrocellulose, LAMINAC (unsaturated polyester crosslinked with styrene), gum arabic, stearic acid, dextrin, PVA, EPIN 828 (difunctional bisphenol A/epichlorohydrin derived liquid epoxy resin), and GILSONITE (natural asphalt). In some aspects, binders, such as SARAN resin (polyvinylidene chloride), can also be added to enhance the robustness of the mix. A binder, if present, is optionally included at an amount of 1% to 10% by weight, optionally 1% to 5% by weight, optionally 2% to 4% by weight.

Some aspects of a biocidal smoke producing composition includes one or more coolants. A coolant serves to lower the burning temperature of the mixture and/or slow down the reaction rate. Illustrative examples of a coolant include nanoscale clay (e.g. bentonite nanoclay (Aldrich), a carbonate (e.g. magnesium carbonate, calcium carbonate, and sodium bicarbonate), diatomaceous earth, and silica. A coolant is optionally present at 0.1% by weight to 10% by weight, or any value or range therebetween.

The individual components (e.g. iodine containing material, metal, binder, coolant, or combinations thereof) when intermixed are optionally dried and compressed under load to reduce the overall volume of the material and optionally to form it into a desired shape to be included with a dispersant or ignition system (e.g. grenade or other). A composition is optionally pressed using a pressure of 500 pounds to 2000 pounds per square inch or any value or range therebetween. The composition is optionally pressed for a time of 1 to 10 seconds or any suitable time to produce the desired pressed composition. The composition may be contacted with a starter mixture sufficient to ignite the thermite reaction or is contacted with a sufficient force to initiate the thermite reaction.

There is also disclosed a design for the use of the biocidal smoke producing composition as provided herein in hand grenades, rifle grenades, smoke pots, floating smoke pots, multiple launch grenades (such as for vehicle decontamination), mortars, shoulder fired missiles, artillery shells, and training aids. This biocidal smoke producing composition could also be used for commercial applications such as first responders for biological releases, and hospital or other building, vehicle, or mobile facility decontamination.

This biocidal smoke producing composition has application in any pressed configuration. When pressed at a loading pressure of 1500 pounds per square inch into a suitable sized canister, the base composition can provide a dense iodine vapor cloud in between 30 and 90 seconds. The total burn time for the hand grenade sized item can be increased beyond 120 seconds by adding additional amounts of a coolant. This composition performs best at an end burning configuration; therefore, varying the length of the canister can also be used to control the burn time.

When pressed into larger canisters suitable for use in indirect fire applications, such as a mortar or artillery shell, or direct fire applications, such as rockets/sub-munition carrying rockets or tank munitions, the composition is pressed at a suitable loading pressure that exceeds the setback force on the canister during the flight to the target area. The base composition has been shown to produce large quantities of biocidal smoke when pressed to pressures of 5000 psi.

Also provided are processes of reducing the viability of a bacterial organism or bacterial spore that is achieved by contacting the bacterial organism or bacterial spore with a biocidal smoke composition as provided herein. A process includes subjecting the biocidal smoke producing composition as provided herein to a force sufficient to induce a reaction between the iodine containing compound and the metal compound thereby producing iodine gas, chlorine gas, or combinations thereof, and contacting the gas to a target organism such as a bacterial organism or spore thereof. The iodine gas, chlorine gas, or both are contacted with the target organism for a time sufficient to reduce the viability of the organism or spore thereof. A contact time is optionally 10 seconds to 10 minutes or more, although typically contact times sufficient to reduce the viability of the target organisms is 90 seconds or less. A target organism has reduced viability if the organism has reduced ability to survive, replicate, infect an organism, or any other marker of organism viability relative to such an organism that is not exposed to a biocidal composition as produced herein.

Illustrative examples of a target organism include but are not limited to *Staphylococcus aureus, Bacillus anthracis, Pseudomonas aeruginosa, Acinetobacter baumannii, Bacillus subtilis, Bacillus globigii, Yersinia pestis, Francisella tularensis, Br. melitensis, Burkholderia pseudomallei, C. botulinum, Bacillus thuringiensis* var. *Kurstaki*, and *Burkholderia mallei*. Optionally, a target organism is a spore of any of the foregoing or other bacterial organism. Optionally a target organism is a spore of *Bacillus anthracis* or *Bacillus thuringiensis* var. *Kurstaki*. Optionally, a target organism is a multicellular organism, optionally a mammal.

The compositions as provided herein have the advantage of excellent stability until a sufficient activation energy is reached to induce a thermite reaction to thereby produce a biocidal smoke that when contacted with a target organism will reduce the viability thereof. The composition is simultaneously safe to handle and transport and can be readily employed in field decontamination operations.

Various aspects of the present invention are illustrated by the following non-limiting examples. The examples are for illustrative purposes and are not a limitation on any practice of the present invention. It will be understood that variations and modifications can be made without departing from the spirit and scope of the invention.

EXAMPLES

Samples of biocidal smoke production compositions were prepared by mixing equal parts of metal powder (Skylighter, Round Hill, Va. or Sigma-Aldrich, St. Louis, Mo.) with iodine pentoxide (Sigma-Aldrich, St. Louis, Mo.), iodine monochloride (Alfa Aesar, Ward Hill, Mass.), or iodine trichloride (Alfa Aesar, Ward Hill, Mass.). Binders were added after mixing of the metal and iodine pentoxide. All mixes were allowed to dry at room temperature thoroughly.

Table 1 provides theoretical iodine vapor generation for several mixtures tested, as calculated by ICT Code software.

TABLE 1

| Metal | Iodine Compound | Iodine Generation (%) |
| --- | --- | --- |
| Brass | Iodine Pentoxide | 36.6 |
| Ferrotitanium (50:50) | Iodine Pentoxide | 49.8 |
| Copper | Iodine Pentoxide | 37.0 |
| Zinc | Iodine Pentoxide | 33.0 |
| Aluminum | Iodine Pentoxide | 42.3 |
| Iron | Iodine Pentoxide | 44.2 |

Mixes were pressed using a Denison Press at 1500 lb dead load with a 3 second dwell in a ½ in mold to form pellets. The pressed samples were placed inside a 2 foot×2 foot×2 foot glass box. Pellets were placed at the center of the box on a steel plate, with biological samples placed to either side. A thermometer was inserted through a port on the side of the box to record temperature.

Approximately 0.5 g of 511 starter mixture (26 pbw (parts by weight) silicon MIL-S-230, 35 pbw potassium nitrate MIL-P-156, 4 pbw charcoal JAN-C-178, 22 pbw black iron oxide MIL-I-275, and 13 pbw aluminum powder MIL-A-512 with a 6% nitrocellulose in acetone binder) was placed on top of the test mixture pellet, with a sufficient length of quickmatch (cotton string impregnated with black powder covered with thin paper to create a tube) taped over top to allow for remote lighting of the sample.

Test mixtures were initiated by fighting the quickmatch. The generated smoke was allowed to contact the biological samples undisturbed for the allotted test time.

The biological samples were prepared on coupons. To prepare the coupons, polycarbonate or steel coupons (3"×1") were washed with 70% ethanol and then rinsed with distilled water. The coupons were then dried and autoclaved at 121° C. for 30 minutes.

Spores of *Bacillus thuringiensis* var. *Kurstaki* were prepared according to established procedures as described in Smith, L S, Wallace, L, Rastogi, V K. 2011. Studies on Speculation Optimization and Characterization of *Bacillus subtilis* Spore Quality. ECBC-TR-899. Cells of *Staphylococcus aureus* were procured from ATCC and grown overnight before use. To inoculate the coupons, an aliquot of 100 µl of working spore stock of *B. thuringiensis* (1E8/ml titer) was added as small droplets across the coupon surface and dried overnight in a BSL-2 cabinet with open surface. On alternate coupons, an aliquot of 50 µl of *S. aureus* broth ($10^7$/ml) was inoculated across the coupon surface as small droplets and the coupons were left open in a BSL-2 cabinet to dry. The coupons were used within an hour of drying (drying was complete in <90 minutes).

The inoculated coupons were placed at either side of the glass box with the biocidal smoke composition placed in the center of the box. The box was sealed on all four sides at the base to provide closed environment for the aerosol. The thermite reaction was ignited as described above and the target organisms exposed overnight. After exposure, the coupons were subjected to spore extraction and analysis.

Spores were extracted from the spore containing coupons by dropping into 20 ml of Tween 80 in a 50 ml sterile tube. The coupons were sonicated for 10 min and then vortexed for 2 minutes. The samples were then serially diluted (ten-fold) in quarter strength Buffered peptone Water before plating on tryptic soy agar (TSA) plates. An aliquot of 100 µl was spread on duplicate TSA plates and the plates were placed in an incubator at 37° C. overnight. The colony-forming units (CFU) were counted the next day on each plates. The average CFU were multiplied with volume factor (10) and dilution factor (1/dilution plated) to estimate viable spore number for each coupon.

Figure 2:
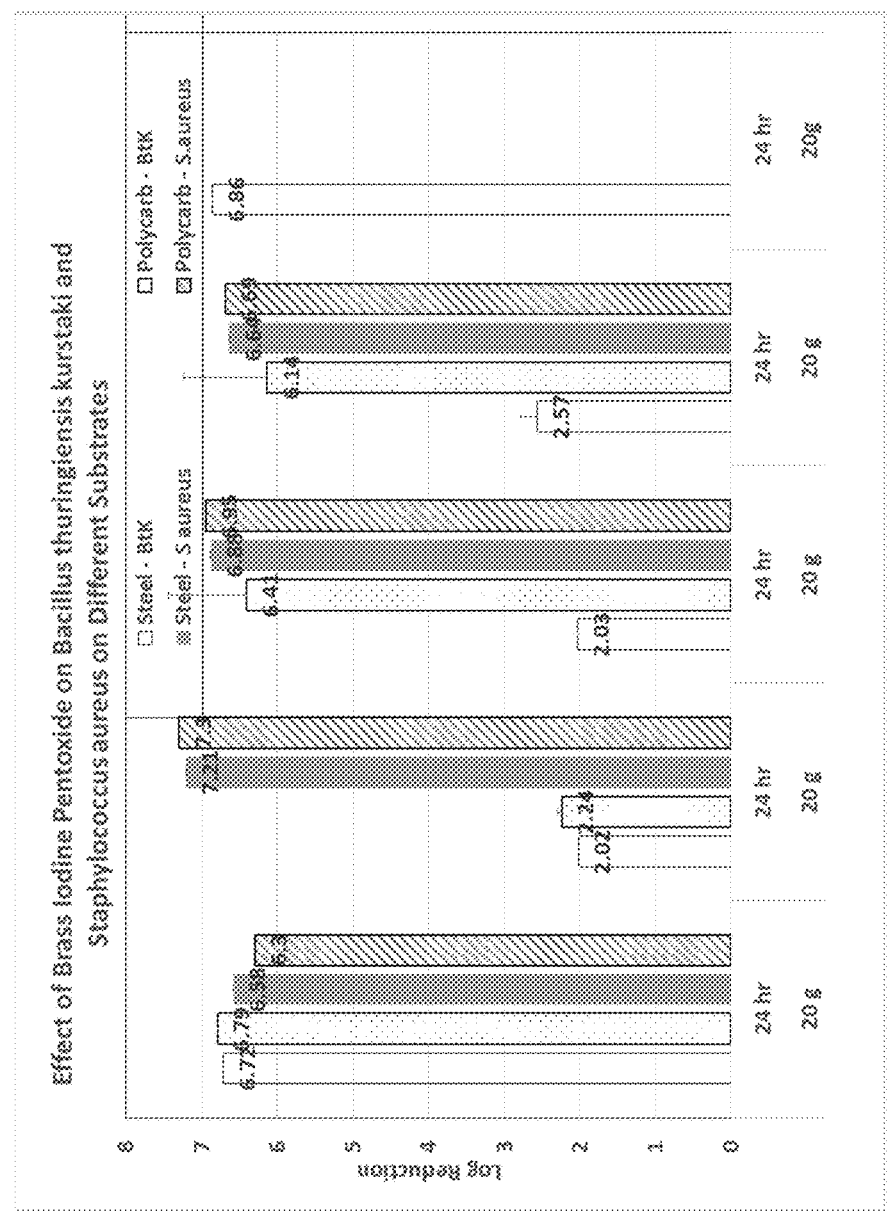
FIG. 2 illustrates the log reduction of *Bacillus thuringiensis* var. *Kurstaki* and *Staphylococcus aureus* relative to control using 20 g of the mixture of brass and iodine pentoxide as the biocidal smoke producing composition and a 24 hour exposure period.

Spore number was calculated for control samples (treated in the same fashion, with the exception of no reactive component in the biocidal aerosol) and test samples, and log density for each sample type was calculated. A 6-log reduction in the number of viable spores (BtK) and/or cells (Sa) on coupon surface is construed as a success criteria for sporicidal or bactericidal efficacy of the tested biocidal aerosol. A spore recovery of >20% (relative to the inoculated number) is also used as performance criteria. The log reduction (LR)=Log density (controls)–Log density (treated) samples. FIG. 1 illustrates the log reduction of *Bacillus thuringiensis* var. *Kurstaki* and *Staphylococcus aureus* relative to control using the mixture of copper and iodine pentoxide as the biocidal smoke producing composition. FIG. 2 illustrates the log reduction of *Bacillus thuringiensis* var. *Kurstaki* and *Staphylococcus aureus* relative to control using the mixture of brass and iodine pentoxide as the biocidal smoke producing composition. Each of the remaining compositions of Table 1 are believed to demonstrate similarly sufficient biocidal activity as measured by reduced viability of cells or spores relative to control.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A biocidal smoke producing composition, comprising:
    an iodine material present in an amount of 50 to 75 percent by weight; and a metal powder present in an amount of 25 to 50 percent, by weight, wherein said metal powder comprises copper, brass, or a combination thereof and wherein said metal powder does not include aluminum;
    the iodine containing material and the metal powder sufficiently reactive to produce a biocidal smoke by a thermite reaction.

2. The composition of claim 1, wherein the iodine material comprises iodine pentoxide, iodine monochloride, iodine trichloride, or combinations thereof.

3. The composition of claim 1, wherein said metal powder is elemental copper.

4. The composition of claim 1, further comprising a binder.

5. The composition of claim 4, wherein said binder comprises polyvinylidene chloride resin.

6. The composition of claim 1, further comprising a coolant.

7. The composition of claim 6, wherein said coolant comprises bentonite.

8. The composition of claim 1, compressed to a sub-detonating loading pressure of 1500 pounds per square inch or greater.

9. The composition of claim 1, wherein said composition is loaded into a dispersant device selected from the group consisting of: a grenade, smoke pot, floating smoke pot, multiple launch grenade, mortar, rocket, sub-munition, missile, tank munition, and artillery shell.

\* \* \* \* \*